United States Patent [19]

Nichol et al.

[11] Patent Number: 4,665,182

[45] Date of Patent: May 12, 1987

[54] BIOPTERIN ANALOGS

[75] Inventors: Charles A. Nichol; John F. Reinhard, Jr., both of Durham; Gary K. Smith, Raleigh; Eric C. Bigham, Chapel Hill, all of N.C.

[73] Assignee: Burroughs Wellcome Co., Rearch Triangle Park, N.C.

[21] Appl. No.: 799,285

[22] Filed: Nov. 19, 1985

Related U.S. Application Data

[63] Continuation of Ser. No. 533,785, Sep. 19, 1983, abandoned.

[30] Foreign Application Priority Data

Sep. 20, 1982 [GB] United Kingdom ............... 8226688

[51] Int. Cl.[4] ................. C07D 475/04; A61K 31/505
[52] U.S. Cl. .................................................. 544/258
[58] Field of Search ..................... 514/249; 544/258

[56] References Cited

U.S. PATENT DOCUMENTS

| 3,959,278 | 5/1976 | Wood et al. | 544/258 |
| 4,073,786 | 2/1978 | Wood et al. | 544/258 |
| 4,540,783 | 9/1985 | Viscontini | 544/258 |
| 4,560,685 | 12/1985 | Roch et al. | 514/249 |

FOREIGN PATENT DOCUMENTS

| 79574 | 5/1983 | European Pat. Off. |
| WO84/04040 | 10/1984 | PCT Int'l Appl. |
| 1293541 | 10/1972 | United Kingdom |

OTHER PUBLICATIONS

Kapatos et al., Science, 212, May 1981, pp. 955-956.
Armarego et al., Aust. J. Chem., 34 (1981), pp. 1921-1933.
Armarego et al., J. Chem. Res., pp. 3911-3914, (1980).
Nagatsu, TIPS, Oct., pp. 276-279, (1981).
Ayling et al., Biochem. and Clin. Asp. of Pteridines, vol. 2, (1983), pp. 147-163.
Bailey et al., Biochemistry, vol. 22, pp. 1790-1798 (1983).

Primary Examiner—Robert Gerstl
Assistant Examiner—Stephen M. Kapner
Attorney, Agent, or Firm—Donald Brown

[57] ABSTRACT

The compounds of formula (I)

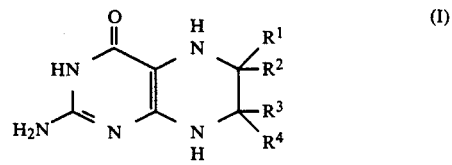

wherein $R^1$ is hydrogen, lower alkyl of 1–4 carbons, lower alkenyl of 2–4 carbons, $-B-X-R^5)_n$, or $-B-Z-B-X-R^5-_n$; $n=0$ when X is halogen or $n=1$ when X is $-O-$, $-NR^6-$ (where $R^6$ is hydrogen or lower alkyl of 1–4 carbons) or $-S(O)q-$ where $q=0$ to 2); B is lower alkanyl (straight or branched) of 1–5 carbons; $R^5$ is hydrogen, aralkyl of 7 to 12 carbons or alkyl of 1–10 carbons; Z is $-O-$, $NR^6-$, or $-S(O)q-$; $R^2$ is hydrogen or lower alkyl of 1–4 carbons or lower alkenyl of 2–4 carbons or either $R^1$ and $R^2$ together with the carbon atom in the pteridine ring structures to which they are attached, form a spirocycloalkyl ring system having 3 to 7 carbon atoms; $R^3$ and $R^4$ are hydrogen or methyl; $R^2$ and $R^3$, together with the carbon atoms in the pteridine ring structure to which they are attached, form a cycloalkyl ring system having 5 to 7 carbon atoms; provided that at least one of $R^1$, $R^2$, $R^3$ and $R^4$ is hydrogen, and further provided that one of $R^1$, $R^2$ and $R^3$, $R^4$ represents gem disubstitution; have been found to selectively cofactor the biological conversion of tyrosine to dopamine, and are useful in the treatment of diseases resulting from a deficiency of dopamine in the brain such as Parkinson's disease. A further aspect of this invention comprises novel compounds of formula (I) defined above with the proviso that when both $R^3$ and $R^4$ are methyl neither $R^1$ and $R^2$ may be methyl, and $R^1$ and $R^2$ may not both be hydrogen, or a pharmaceutically acceptable salt thereof.

2 Claims, No Drawings

BIOPTERIN ANALOGS

This is a continuation of co-pending application Ser. No. 533,785 filed on 9/19/83, now abandoned.

The present invention relates to a series of pteridines known as pterins which are analogs of biopterin, to pharmaceutical formulations containing them, to processes for their preparation and to the use thereof in human medicine. More specifically the invention relates to certain biopterin analogs and their use in the treatment of Parkinsonism and other diseases caused by a deficiency of catecholamines in the brain and the peripherial nervous system.

The invention accordingly provides in a first aspect the pterin compounds of formula (I) below together with pharmaceutically acceptable salts thereof for use in human medicine.

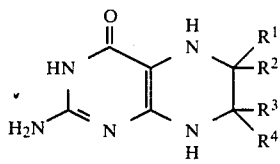

wherein $R^1$ is hydrogen, lower alkyl of 1-4 carbons, lower alkenyl of 2-4 carbons, —B—X—($R^5)_n$, or —B—Z—B—X—($R^5)_n$, $n=0$ when X is halogen or $n=1$ when X is —O—, —$NR^6$— (where $R^6$ is hydrogen or lower alkyl of 1-4 carbons) or —$S(O)_q$— (where $q=0$ to 2); B is lower alkanyl (straight or branched) of 1-5 carbons; $R^5$ is hydrogen, aralkyl of 7 to 12 carbons or alkyl of 1-10 carbons; Z is —O—, —$NR^6$—, or —$S(O)_q$—; $R^2$ is hydrogen or lower alkyl of 1-4 carbons or lower alkenyl of 2-4 carbons or either $R^1$ and $R^2$ together with the carbon atom in the pteridine ring structures to which they are attached, form a spirocycloalkyl ring system having 3 to 7 carbon atoms; $R^3$ and $R^4$ are hydrogen or methyl; $R^2$ and $R^3$, together with the carbon atoms in the pteridine ring structure to which they are attached, form a cycloalkyl ring system having 5 to 7 carbon atoms; provided that at least one of $R^1$, $R^2$, $R^3$ and $R^4$ is hydrogen, and further provided that one of $R^1$, $R^2$ and $R^3$, $R^4$ represents gem disubstitution; or a pharmaceutically acceptable salt thereof or a bioprecursor thereof.

A further aspect of the invention comprises the novel compounds of formula (I) as defined herein with the additional proviso that when both $R^3$ and $R^4$ are methyl neither $R^1$ nor $R^2$ may be methyl, and $R^1$ and $R^2$ may not both be hydrogen.

It is generally accepted that certain substances known as neurotransmitters are required at the microscopic regions, known as synapses, between the terminals of nerve cells, neurons, to transmit the nerve impulses through the body.

Over thirty substances are known or suspected to be neurotransmitters and each has a characteristic excitatory or inhibitory effect on neurons. Excesses or deficiencies of these transmitters can be manifested as moderate to severe neurological or mental disorders. While neurons are spread throughout the body, imbalance of the neurotransmitters at the synapses of the neurons in the brain are by far the most critical and produce the most pronounced effects.

Of the numerous neurotransmitters known or thought to be operating at synapses a smaller group collectively known as biogenic amines have received considerable study. Particularly important members of this group are the catecholamines such as dopamine and norepinephrine (noradrenaline) and the indole amine, serotonin.

Knowledge of the chemical pathology of neurological disorders has expanded tremendously during the last two decades. For example, there have been described neurological disorders whose symptoms can be associated with decreases in the number of catecholamine molecules released at certain synaptic sites. As a category, they may be thought of as 'catecholamin-deficiency disorders'. One example is Parkinson's disease (also known as Parkinsonism), where a deficiency in brain dopamine has been linked with the symptoms of rigidity, tremor and akinesia. Another example is chronic preganglionic autonomic insufficiency known as the Shy-Drager syndrome which is associated with both peripheral sympathetic dysfunction—resulting in syncope and a degeneration of brain neurons in the basal ganglia, which accounts for the tremor and akinesia observed with this disease. The peripheral sympathetic dysfunction is thought to be due to decreased formation and release of the pressor catecholamine norepinephrine, while the rigidity and akinesia is thought to reflect a loss of brain dopamine containing neurons. In all of these cases, the catecholamines, whose levels are diminished, are formed through the action of tyrosine hydroxylase which is rate-limiting for their formation. This enzyme requires tyrosine, oxygen and a reduced pterin cofactor, tetrahydrobiopterin ($BH_4$), for activity. While oxygen and tyrosine are not normally limiting for tyrosine hydroxylase, the levels of BH are normally well below the levels required to saturate this enzyme. In fact, the levels of this cofactor are severely diminished in Parkinson's disease and in the Shy-Drager syndrome.

For Parkinson's disease, as an example of a catecholamine deficiency disorder, the most common therapy has been to administer the amino acid precursor of dopamine, 3,4-dihydroxyphenylalanine (DOPA). Although DOPA administration produces symptomatic improvements in Parkinson's disease, the therapy is not without certain difficulties. Indeed, the large quantities of DOPA, which are administered, form dopamine at sites in the brain where the compound is not normally found. This results in a proportion of DOPA-treated patients developing psychotic side effects. Consequently, the application of this therapy is being reserved for the most serious cases of Parkinson's disease.

Tyrosine administration has also been reported to produce limited improvements in Parkinson's disease. The advantage of tyrosine therapy is that it promotes catechol synthesis at sites where catecholamines are normally found. However, tyrosine levels in brain are only slightly below the point of saturation of tyrosine hydroxylase. Thus, tyrosine can produce only limited benefit. In contrast, the pterin cofactor, tetrahydrobiopterin ($BH_4$), is well below saturating levels for tyrosine hydroxylase, both in brain and in peripheral nervous tissue in normal individuals (Nagatsu, T., *Neurochem. Intern,* 5, 27 (1983)). Further, as stated above, the level of this cofactor in Parkinson's disease and Shy-Drager syndrome patients is depressed even below this subsaturating level. Thus, increased catechol synthesis can be affected by reversing this deficit. Administration of $BH_4$ has been shown to nearly double striatal dopamine synthesis, as well as noradrenaline synthesis in peripheral nerves. In fact, BH4 administration has been reported to improve the symptoms of Parkinson's disease (Narabayashi, H.; Kondo, T.; Nagatsu, T.; Sugimoto, T. and Matsuura, S., *Proc. Japan Acad.*, 58. Ser. B 283 (1982)). This natural cofactor is however, expensive, unstable, and it penetrates brain poorly (Kaufman, S.; Kapatos, G.; McInnes, R.; Schulman, J. and Rizzo, W., *Pediatrics*, 70, 376 (1982)). Moreover, since BH4 is not selective for dopamine production, it would logically be expected to increase the synthesis of serotonin in the brain and in the small intestine.

Quite unexpectedly, the compounds of formula (I), described herein, do not act as co-factors for tryptophan hydroxylase the rate-limiting enzyme for serotonin biosynthesis, but retain high activity for tyrosine hydroxylase, which would not have been predicted based upon studies performed with the pterin co-factors previously tested. By promoting the hydroxylation of tyrosine, i.e., conversion to dopamine via DOPA, these compounds lessen the symptoms of Parkinson's disease, orthostatic hypotension (Shy-Drager variant), muscular dystonia and other disorders arising from a deficiencies of catecholamines. In contrast to the natural cofactor BH4, the gem-disubstituted compounds of formula (I) are more stable in vivo and gain entry into the brain more easily.

Compounds of formula (I) and their salts may be synthesized by methods known in the art of synthesis of compound having analogous structures.

A method of preparing compounds of formula (I) wherein $R^2$ or $R^4$ is hydrogen comprises reacting a compound of formula (II) or (IIA) respectively with a reducing agent capable of donating hydrogens such as H2/catalyst, sodium cyanoborohydride or sodium borohydride all in a suitable solvent under conditions normally used for these reagents. Compounds of formula (I) may also be prepared by reduction in vitro or in vivo, of compounds of formula (II) or (IIA) using an appropriate enzyme such as dihydrofolic reductase.

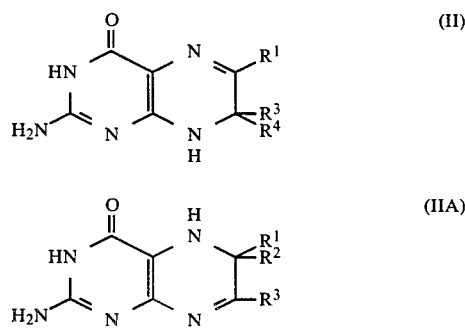

Compounds of formula (I) when $R^1$ and $R^3$ are hydrogen can be prepared by chemical or enzymatic reduction of compounds of formula (III) by a similar procedure to that described above. Compounds of formula (III) may be prepared by methods known to those skilled in the art (see for example UK Patent Nos. 1303171, 1363064 and 1454165 and *Aust. J. Chem.*, 33 34 (1921)).

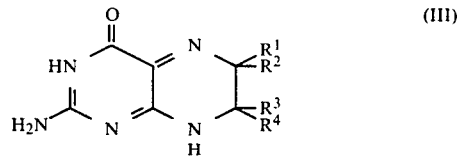

Compounds of this invention may be used to treat Parkinson's disease orthostatic hypotension (Shy-Drager Syndrome), muscular dystonia and other disorders which arise from deficiencies of available catecholamines at the pre-synaptic sites of neuronal junctions.

The compounds of formula (I) found to be particularly active are:

(+ −)-2-Amino-5,6,7,8-Tetrahydro-6-Methoxymethyl-7,7-Dimethyl-4(3H)Pteridinone Dihydrochloride, (+ −)-2-Amino-5,6,7,8-tetrahydro-7-hydroxymethyl-6,7-dimethyl-4(3H)-pteridinone, (+ −)-2-Amino-5,6,7,8-tetrahydro-6-hydroxymethyl-7,7-dimethyl-4(3H)-pteridinone dihydrochloride (+,−)-2-Amino-6-butoxymethyl-5,6,7,8-tetrahydro-7,7-dimethyl-4(3H)-pteridinone dihydrochloride hemihydrate, (+,−)-2-Amino-5,6,7,8-tetrahydro-6-isopentyloxymethyl-7,7-dimethyl-4(3H)-pteridinone dihydrochloride, (+,−)-2-Amino-5,6,7,8-tetrahydro-7,7-dimethyl-6-octyloxymethyl-4(3H)-pteridinone dihydrochloride, (+,−)-2-Amino-5,6,7,8-tetrahydro-7,7-dimethyl-6-pentoxymethyl-4(3H)-pteridinone dihydrochloride, (+,−)-2-Amino-6-(3-cyclohexylpropoxymethyl)5,6,7,8-tetrahydro-7,7-dimethyl-4(3H)-pteridinone dihydrochloride, (+,−)-2-Amino-5,6,7,8-tetrahydro-7,7-dimethyl-6-(3-phenylpropoxymethyl)-4(3H)-pteridinone dihydrochloride, (+,−)-2-Amino-5,6,7,8-tetrahydro-6-isopropoxymethyl-7,7-dimethyl-4(3H)-pteridinone dihydrochloride one-quarter hydrate, (+,−)-2-Amino-5,6,7,8-tetrahydro-7,7-dimethyl-6-propoxymethyl-4(3H)-pteridinone dihydrochloride, (+,−)-2-Amino-5,6,7,8-tetrahydro-7,7-dimethyl-6-propyl-4(3H)-pteridinone dihydrochloride, (+,−)-2-Amino-5,6,7,8-tetrahydro-6-isopropyl-7,7-dimethyl(4(3H)-pteridinone dihydrochloride, (+,−)-2-Amino-5,6,7,8-tetrahydro-6-(2-hydroxyethyl)-7,7-dimethyl-4(3H)-pteridinone dihydrochloride, (6RS)-2-Amino-5,6,7,8-tetrahydro-6-(1-hydroxy-(1RS)-ethyl)-7,7-dimethyl-4(3H)-pteridinone dihydrochloride, (+,−)-2-Amino-5,6,7,8-tetrahydro-6,6,7-trimethyl-4(3H)-pteridinone hydrochloride, (+,−)-2-Amino-6-ethyl-5,6,7,8-tetrahydro-7,7-dimethyl-4(3H)-pteridinone dihydrochloride hemihydrate and (+,−)-2-Amino-6-ethoxymethyl-5,6,7,8-tetrahydro-7,7-dimethyl-4(3H)-pteridinone dihydrochloride ¾ hydrate.

The amount of the active compound, i.e. a compound of formula (I), required for use in the above disorder will, of course, vary with the route of administration, the condition being treated, and the person undergoing treatment, but is ultimately at the discretion of the physician. However, a suitable dose for treating these disorders is in the range of from 0.5 to 20 mg per kilogram body weight per day preferably from 1 to 10 mg/kg body weight per day, most preferably from 2 to 7 mg/kg body weight per day, a typical preferred dose is 5 mg/kg body weight per day.

The desired dose is preferably presented as between one and four subdoses administered at appropriate intervals throughout the day. Thus where three sub-doses are employed each will lie in the range of from 0.17 to 6.7 mg/kg body weight; a typical dose for a human recipient being 1.7 mg/kg body weight.

If desirable the dopamine precursor, tyrosine, may be administered concurrently with a compound of formula (I) at the rate of 25 mg/kg to 1000 mg/kg body weight. Tyrosine may be given in the same pharmaceutical formulation, e.g., tablet or capsule, as a compound of formula (I) or in a separate pharmaceutical formulation within half an hour of the administration of a compound of formula (I).

While it is possible for the active compound or compounds to be administered alone as the raw chemicals, it is preferable to present the active compound or compounds as pharmaceutical formulations. Formulations of the present invention comprise a compound of formula (I) together with one or more pharmaceutically acceptable carriers thereof and optionally any other active therapeutic ingredients.

The carrier(s) must be pharmaceutically acceptable in the sense of being compatible with the other ingredients of the formulation and not deleterious to the recipient thereof. The other therapeutic ingredient(s) may include dopamine precursors.

The formulations include those suitable for oral, rectal or parenteral (including subcutaneous, intramuscular, and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a finely divided solid carrier and then, if necessary, shaping the product into the desired formulations or packaging in a suitable container.

Formulations of the present invention suitable for oral administration may be presented as discrete units such as capsules, cachets, tablets or lozenges, each containing a predetermined amount of the active compound(s); as a powder or granules; or a suspension in a non-aqueous liquid such as a syrup, an elixir, an emulsion or a draught. The active compound(s) may also be presented as a bolus or depot formulation.

A tablet may be made by compression or molding, optionally with one or more accessory ingredients. Compressed tablets may be prepared by compressing in a suitable machine, the active compound being in a free-flowing form such as a powder or granules, optionally mixed with a binder, lubricant, inert diluent, surface active or dispersing agent. Molded tablets may be made by molding in a suitable machine, comprising a mixture of the powdered active compound(s) with any suitable carrier.

Formulations for rectal administration may be presented as a suppository with a usual carrier such as cocoa butter.

Formulations suitable for parenteral administration can be made sterile and packed as dry solids in sealed sterile containers. At the time of parenteral administration a specified amount of sterile water is added to the drug formulation and the resulting solution is administered to the patient with a minimum of delay since the compounds of formula (I) tend to be unstable. In aqueous solution over a period of time.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

Compounds of the formula (I) are particularly useful in increasing the synthesis of dopamine and norepinephrine in mammals such as rats and humans. Such effects are produced by administration preferably orally or parenterally.

The following examples are provided by the way of illustration of the present invention and should in no way be construed as a limitation thereof.

EXAMPLE 1

(+ −)-2-Amino-5,6,7,8-Tetrahydro-6-Methoxymethyl-7,7-Dimethyl-4(3H)Pteridinone Dihydrochloride A mixture of 2-amino-7,8-dihydro-6-methoxymethyl-7,7-dimethyl-4(3H)-pteridinone, 0.10 g and platinum oxide (prereduced) 0.015 g, in 6 mL of 2N HCl was hydrogenated at 1 atm $H_2$ at room temperature for 2.5 hr. the mixture was filtered, and the filtrate was evaporated. This crude product was recrystallized from 6N HCl/MeCN to yield 2-amino-5,6,7,8-tetrahydro-6-methoxymethyl-7,7-dimethyl-4(3H)-pteridinone hydrochloride 0.089 g as a white solid, m.p. 214°–300° C. (dec), 76% of theoretical yield.

Elemental analysis: Calc'd. for $C_{10}H_{17}N_5O_2.2HCl$: C, 38.47, H, 6.13, N, 22.43; Cl, 22.71. Found: C, 38.33; H, 6.16; N, 22.34; Cl, 22.71.

EXAMPLES 2 AND 3

The following compounds were prepared from their corresponding precursors by the method described in example 1.

2. (+ −)-2-Amino-5,6,7,8-tetrahydro-7-hydroxymethyl-6,7-dimethyl-4(3H)-pteridinone m.p. >300° C.

Elemental analysis: Calc'd. for $C_9H_{15}N_5O.1/20$ $C_9H_{13}N_5O$ 23/20 HCl.11/25 $C_3H_8O.3/20$ $H_2O$: C, 42.37; H, 6.79; N, 23.85; Cl, 13.10. Found C, 42.41; H, 6.75; N, 23.89; Cl, 13.10.

3. (+ −)- 2-Amino-5,6,7,8-tetrahydro-6-hydroxymethyl-7,7-dimethyl-4(3H)-pteridinone dihydrochloride m.p. 200° C. (dec).

Elemental analysis: Calc'd. for $C_9H_{15}N_5O_2.2HCl$: C, 36.25; H, 5.75; N, 23.49; Cl, 23.78. Found: C, 36.13; H, 5.77; N, 23.42; Cl, 23.65.

4. (+,−)-2-Amino-6-butoxymethyl-5,6,7,8-tetrahydro-7,7-dimethyl-4(3H̲)-pteridinone dihydrochloride hemihydrate A solution of 2-amino-6-butoxymethyl-7,8-dihydro-7,7-dimethyl-4(3H̲)-pteridinone (153 mg, 0.548 mmol) in trifluoroacetic acid (3 mL) was hydrogenated over platinum oxide (11.3 mg) under 1 atm of $H_2$ at room temperature for 15 min. To the mixture was added 6N HCl (about 3 mL) and the product isolated as in Example 2 to yield 0.15 g (75%) of a white powder: m.p. dec. above 200° C.; IR (KBr) 2960, 2870, 1650, 1570, 1450, 1400, 1180, 1120, 735 cm$^{-1}$; UV (0.1N HCl) $\lambda_{max}$: 217 nm (ϵ) (19900), 263.5 (14300), λmin: 239 (4000); $^1$H-

NMR (DMSO-d$_6$) δ from TMS: 0.88 (m, 3H, Me), 1.14 (S, 3H, Me), 1.28 (s, 3H, Me), 1.44 (M, 4H, CH$_2$CH$_2$), 3.44 (M, 5H, C-6H, CH$_2$OCH$_2$), rest exchanged.

Elemental Analysis: Calc'd. for C$_{13}$H$_{23}$N$_5$O$_2$ 2HCl ½H$_2$O: C, 42.98; H, 7.21; N, 19.28; Cl, 19.52. Observed: C, 42.95; H, 7.22; N, 19.48; Cl, 19.51.

EXAMPLES 5 TO 17

The following compounds were prepared from their corresponding precursors by the method described in Example 4.

5. (+,−)-2-Amino-5,6,7,8-tetrahydro-6-isopentyloxymethyl-7,7-dimethyl-4(3H)-pteridinone dihydrochloride M.p. dec. above 190° C.

Elemental Analysis: Calc'd. for C$_{14}$H$_{25}$N$_5$O$_2$ 2 HCl: C, 45.65; H, 7.39; N, 19.02; Cl, 19.25. Observed: C, 45.53; H, 7.40; N, 19.00; Cl, 19.11.

6. (+,−)-2-Amino-5,6,7,8-tetrahydro-7,7-dimethyl-6-octyloxymethyl-4(3H)-pteridinone dihydrochloride M.p. dec. above 200° C.

Anal. calc'd. for C$_{17}$H$_{31}$N$_5$O$_2$ 2 HCl: C, 49.75; H, 8.10; N, 17.07; Cl, 17.28. Found: C, 49.68; H, 8.13; N, 17.07; Cl, 17.26.

7. (+,−)-2-Amino-5,6,7,8-tetrahydro-7,7-dimethyl-6-pentoxymethyl-4(3H)-pteridinone dihydrochloride M.p. dec. above 190° C.

Elemental Anlaysis: Calc'd. for C$_{14}$H$_{25}$N$_5$O$_2$ 2 HCl: C, 45.65; H, 7.39; N, 19.02; Cl, 19.25. Found: C, 45.63; H, 7.43; N, 19.02; Cl 19.19.

8. (+,−)-2-Amino-6-(3-cyclohexylpropoxymethyl)-5,6,7,8-tetrahydro-7,7-dimethyl-4(3H)-pteridinone dihydrochloride M.p.=216°-221° C. (dec).

Elemental Analysis: Calc'd. for C$_{18}$H$_{31}$N$_5$O$_2$ 2 HCl: C, 51.18; H, 7.87; N, 16.58; Cl, 16.79. Found: C, 50.97; H, 7.91; N, 16.52; Cl, 16.38.

9. (+,−)-2-Amino-5,6,7,8-tetrahydro-7,7-dimethyl-6-(3-phenylpropoxymethyl)-4(3H)-pteridinone dihydrochloride This compound was made by NA BH$_3$CN reduction rather than Pt/H$_2$/TFA M.p.=194°-200° C. (dec).

Anal. calc'd for C$_{18}$H$_{25}$N$_5$O$_2$ 2 HCl: C, 51.92; H, 6.54; N, 16.82; Cl, 17.03. Found: C, 51.73; H, 6.57; N, 16.72; Cl, 17.03.

10. (+,−)-2-Amino-5,6,7,8-tetrahydro-6-isopropoxymethyl-7,7-dimethyl-4(3H)-pteridinone dihydrochloride one-quarter hydrate M.p.=190°-192° C. (dec)

Anal. calc'd. for C$_{12}$H$_{21}$N$_5$O$_2$ 2 HCl ¼H$_2$O: C, 41.81; H, 6.87; N, 20.31; Cl, 20.57. Found: C, 41.79; H, 6.89; N, 20.27; Cl, 20.59.

11. (+,−)-2-Amino-5,6,7,8-tetrahydro-7,7-dimethyl-6-propoxymethyl-4(3H)-pteridinone dihydrochloride Anal. calc'd. for C$_{12}$H$_{21}$N$_5$O$_2$ 2 HCl: C, 42.36; H, 6.81; N, 20.58.

Found C, 42.31; H, 6.81; N, 20.53.

12. (+,−)-2-Amino-5,6,7,8-tetrahydro-7,7-dimethyl-6-propyl-4(3H)-pteridinone dihydrochloride UV (0.1N HCl) λ$_{max}$: 263.5, 214 nm; λmin: 238.5 nm.

13. (+,−)-2-Amino-5,6,7,8-tetrahydro-6-isopropyl-7,7-dimethyl-4(3H)-pteridinone dihydrochloride UV (0.1N HCl) λ$_{max}$: 264, 217 nm; λmin: 239 nm.

14. (+,−)-2-Amino-6-ethyl-5,6,7,8-tetrahydro-7,7-dimethyl-4(3H)-pteridinone dihydrochloride hemihydrate

M.P.=206°-216° C.

Anal. calc'd for C$_{10}$H$_{17}$N$_5$O 2 HCl ½H$_2$O: C, 39.35; H, 6.60; N, 22.95; Cl, 23.23. Found: C, 39.11; H, 6.51; N, 22.95; Cl, 23.26.

15. (+,−)-2-Amino-6-ethoxymethyl-5,6,7,8-tetrahydro-7,7-dimethyl-4(3H)-pteridinone dihydrochloride ¾ hydrate M.p.=203°-207° C. (dec)

Anal. calc'd for C$_{11}$H$_{19}$N$_5$O$_2$ 2 HCl ¾H$_2$O: C, 38.89; H, 6.68; N, 20.61; Cl, 20.87. Found: C, 38.92; H, 6.64; N, 20.72; Cl, 20.77.

16. (+,−)-2-Amino-5,6,7,8-tetrahydro-6-(2-hydroxyethyl)-7,7-dimethyl-4(3H)-pteridinone dihydrochloride UV (0.1N HCl) 264.5 (13700), 217 nm (18500); IR (KBr) 1670 cm$^{-1}$; NMR (DCl/D$_2$O) 0.98 (s, Me), 0.97 (s, Me), 1.57 (m, CH$_2$), 3.36 (m, C-6H, CH$_2$O);

Elemental analysis: Calc'd for C$_{10}$H$_{17}$N$_5$O$_2$ 2HCl 3/2 H$_2$O: C, 35.41; H, 6.54; N, 20.65; Cl, 20.90. Found: C, 35.23; H, 6.28; N, 20.64; Cl, 20.71.

17. (6RS)-2-Amino-5,6,7,8-tetrahydro-6-(1-hydroxy-(1RS)-ethyl)-7,7-dimethyl-4(3H)-pteridinone dihydrochloride Made by reduction of the 6-acetyl intermediate. UV (0.1N HCl): 265 nm (13600), 216 (19800); IR (KBr): 1665 cm$^{-1}$.

NMR (0.1N DCl/D$_2$O): 0.8-1.1 (m, 3 Me's), 2.11 (s, ⅓H, 6-acetyl), 2.98 (d, J-3.9Hz, ⅓H, 6-H, erythro), 3.15 (d, J=4.4 Hz, ⅔H, 6-H, threo), 3.88 (M, OCH). Contains 10% 6-acetyl analog.

Elemental analysis: Calc'd for C$_{10}$H$_{17}$N$_5$O$_2$ 2HCl ½H$_2$O: C, 37.39; H, 6.28; N, 21.80; Cl, 22.07. Found: C, 37.52; H, 6.28; N, 21.75; Cl, 22.13.

18. (+,−)-2-Amino-5,6,7,8-tetrahydro-6,6,7-trimethyl-4(3H)-pteridinone hydrochloride The intermediate, 2-amino-7,8-dihydro-6,7-dimethyl-4(3H)-pteridinone was prepared according to Viscontini (*Methods in Enz.*, XVIII, p 704). This compound was treated with methyl lithium under conditions described by Armarego and Waring (*Aust. J. Chem.* 1981, 34, 1921). M.P.>300° C.; UV (0.1N HCl): 266 nm (15300); IR (KBr): 1600, 1629, and 1660 cm$^{-1}$; NMR (DMSO-d$_6$): 1.07 δ (s, Me), 1.09 (d, J=6.3 Hz, Me), 1.34 (s, Me), 3.4 (q, J=6.3 Hz, H-7), 3.5 (br, NH) 6.76 (br s, NH$_2$), 7.4 (br s, NH), 9.9 (br, NH), and 10.8 (br s, NH).

Anal. calc'd for C$_9$H$_{15}$N$_5$O HCl: C, 43.99; H, 6.56; N, 28.50; Cl, 14.43. Found: C, 43.88; H, 6.57; N, 28.47; Cl, 14.49.

EXAMPLE 19

Biological Data

Tyrosine hydroxylase was partially purified through a 25-45% ammonium sulfate fraction. Specific activity of this preparation with tetrahydrobiopterin was 4.0 nmole/mg protein (min). The enzyme was assayed by a modification of the method of Nagatsu, T., Levitt, M., and Udenfriend, S. (*Anal. Biochem.* 9, 122, (1964)) where the Dowex chromatography step was replaced by a charcoal.

Tryptophan hydroxylase was assayed according to a modification of the method of Renson J., et al (*Biochem. Biophys. Acta* 25: 504 (1966)). The preparation of tryptophan hydroxylase was a crude 30,000 xg supernatant which had been desalted on a Sephadex G-25 (Trade Name) column (Boadle-Biker, M. C., *Biochem Pharmacol.* 28: 2129 (1979). The specific activity of this tryptophan hydroxylase, using BH$_4$ a cofactor, was approximately 100 pmol product per milligram protein per minute at 37°.

Phenylalanine hydroxylase was measured as described by Shiman, R. et al., (*J. Biol. Chem.* 254: 11300 (1979)) except that the product of the reaction (tyrosine) was measured fluorometrically using the method of Waalkes, T. P. and Udenfriend, S. (*J. Lab. Clin. Med.* 50: 733 (1957). Phenylalanine hydroxylase was prepared from rat liver using hydrophobic chromatography (Shiman, R. et al. (*J. Biol. Chem.* 254: 11,300 (1979)). The specific activity of the enzyme, using $BH_4$ as the co-factor, was 1.0 μmol/mg protein per minute at 37°.

TABLE I

Hydroxylase Cofactor Activity of Various Pterins

| Compound of Formula (I) | | | | $V_{max}$ (%) | | |
|---|---|---|---|---|---|---|
| $R^1$ | $R^2$ | $R^3$ | $R^4$ | Tyrosine Hydroxylase | Tryptophan Hydroxylase | Phenylalanine Hydroxylase |
| Tetrahydrobiopterin ($BH_4$) | | | | 100 | 100 | 100 |
| $CH_2$—O—$CH_3$, | H, | $CH_3$, | $CH_3$ | 138 | 0 | 5 |
| $CH_2OH$, | H, | $CH_3$, | $CH_3$ | 102 | 0 | 5 |
| $CH_3$, | H, | $CH_3$, | $CH_3$ | 54 | 0 | 43 |
| $CH_3$, | H, | $CH_3$, | $CH_2OH$ | 25 | 0 | 3 |
| H, | H, | $CH_3$, | $CH_3$ | 83 | 0 | 5 |
| $CH(OH)CH_3$, | H, | $CH_3$, | $CH_3$ | 32 | — | — |
| $CH_2CH_2OH$, | H, | $CH_3$, | $CH_3$ | 20 | — | — |
| $CH_3$, | H, | $CH_3$, | $CH_3$ | 20 | — | — |

Numbers are percent of maximal velocities obtained with $BH_4$. Enzyme assays were performed as described in the text.

EXAMPLE 20

Pharmaceutical Formulations

| A. Capsule | |
|---|---|
| Ingredient | Amount per Capsule (mg) |
| Compound I | 325.0 |
| Ascorbic Acid | 174.0 |
| Corn Starch | 100.0 |
| Stearic Acid | 27.0 |

The finely ground active compound was mixed with the powdered excipients lactose, corn starch and stearic acid and packed into gelatin capsule.

| B. Tablet | |
|---|---|
| Ingredient | Amount per tablet (mg) |
| Compound I | 325.0 |
| Ascorbic Acid | 125.0 |
| Corn Starch | 50.0 |
| Polyvinylpyrrolidone | 3.0 |
| Stearic Acid | 1.0 |
| Magnesium stearate | 1.0 |

The active compound was finely ground and intimately mixed with the powdered excipients lactose, corn starch, polyvinylpyrrolidone, magnesium stearate and stearic acid. The formulation was then compressed to afford one tablet weighing 505 mg.

| A. Suppository | |
|---|---|
| Ingredient | Amount per suppository |
| Compound I | 325.0 mg |
| Butylated Hydroxy Toluene (BHT) | 25.0 mg |
| Cocoa Butter, q.s. or Wecobee Base | 2.0 g |

Wecobee is the trade name of a hydrogenated carboxylic acid.

We claim:

1. A compound which is selected from:

(+−)-2-Amino-5,6,7,8-Tetrahydro-6-Methoxymethyl-7,7-Dimethyl-4(3H)Pteridinone Dihydrochloride, (+−)-2-Amino-5,6,7,8-tetrahydro-7-hydroxymethyl-6,7-dimethyl-4(3H)-pteridinone, (+−)-2-Amino-5,6,7,8-tetrahydro-6-hydroxymethyl-7,7-dimethyl-4(3H)-pteridinone dihydrochloride (+,−)-2-Amino-6-butoxymethyl-5,6,7,8-tetrahydro-7,7-dimethyl-4(3H)-pteridinone dihydrochloride hemihydrate, (+,−)-2-Amino-5,6,7,8-tetrahydro-6-isopentyloxymethyl-7,7-dimethyl-4(3H)-pteridinone dihydrochloride, (+,−)-2-Amino-5,6,7,8-tetrahydro-7,7-dimethyl-6-octyloxymethyl-4(3H)-pteridinone dihydrochloride, (+,−)-2-Amino-5,6,7,8-tetrahydro-7,7-dimethyl-6-pentoxymethyl-4(3H)-pteridinone dihydrochloride, (+,−)-2-Amino-5,6,7,8-tetrahydro-7,7-dimethyl-6-(3-phenylpropoxymethyl)-4(3H)-pteridinone dihydrochloride, (+,−)-2-Amino-5,6,7,8-tetrahydro-6-isopropoxymethyl-7,7-dimethyl-4(3H)-pteridinone dihydrochloride one-quarter hydrate, (+,−)-2-Amino-5,6,7,8-tetrahydro-7,7-dimethyl-6-propoxymethyl-4(3H)-pteridinone dihydrochloride, (+,−)-2-Amino-5,6,7,8-tetrahydro-6-(2-hydroxyethyl)-7,7dimethyl-4(3H)-pteridinone dihydrochloride, (6RS)-2-Amino-5,6,7,8-tetrahydro-6-(1-hydroxy-(1RS)-ethyl)-7,7-dimethyl-4(3H)-pteridinone dihydrochloride, (+,−)-2-Amino-6-ethoxymethyl-5,6,7,8-tetrahydro-7,7-dimethyl-4(3H)-pteridinone dihydrochloride ¾ hydrate.

2. (+,−)-2-Amino-6-(3-cyclohexylpropoxymethyl)5,6,7,8-tetrahydro-7,7-dimethyl-4(3H)-pteridinone or a pharmaceutically acceptable salt thereof.

* * * * *